United States Patent [19]

Tatsuoka et al.

[11] Patent Number: 5,041,444
[45] Date of Patent: Aug. 20, 1991

[54] BENZOXEPIN DERIVATIVES

[75] Inventors: Toshio Tatsuoka, Nishinomiya; Makoto Shibata, Takatsuki, both of Japan

[73] Assignee: Suntory Limited, Osaka, Japan

[21] Appl. No.: 490,327

[22] Filed: Mar. 8, 1990

[30] Foreign Application Priority Data

Mar. 15, 1989 [JP] Japan .................................. 1-61040

[51] Int. Cl.$^5$ .................... A61K 31/50; A61K 31/505; A61K 31/44; A61K 31/415
[52] U.S. Cl. .................................... 514/254; 514/256; 514/337; 514/397; 514/422; 514/444; 514/450; 549/355; 549/60; 548/525; 548/336; 544/238; 544/333; 544/405; 546/269
[58] Field of Search .................. 549/355, 60; 548/525, 548/336; 544/238, 333, 405; 546/269; 514/254, 397, 450

[56] References Cited

U.S. PATENT DOCUMENTS 4,766,212 8/1988 Freedman et al. .................. 544/101

Primary Examiner—John M. Ford
Attorney, Agent, or Firm—Burns, Doane, Swecker & Mathis

[57] ABSTRACT

A benzoxepin derivative represented by the formula (I):

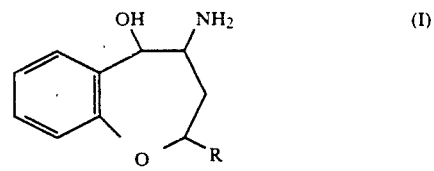

wherein R represents a heterocyclyc group, and salts thereof; a process for production thereof comprising the steps of reducing an oxime represented by the formula (V):

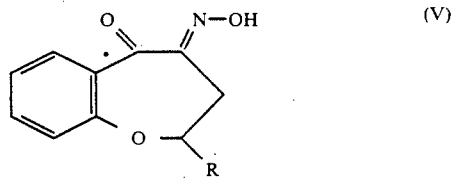

wherein R has the same meaning as defined in the formula (I), and hydrolyzing the intermediate produced of the above reduction; and pharmaceuticals comprising the compound (I).

4 Claims, No Drawings

BENZOXEPIN DERIVATIVES

BACKGROUND OF THE INVENTION

1. Field of the Invention

The present invention relates to benzoxepin derivatives, process for the production of the benzoxepin, and a pharmaceutical preparation containing same.

2. Description of the Related Art

There are two types diabetes known, i.e., an insulin-dependent type I and an insulin-non-dependent type II. The type II diabetes, which comprises 90% of all diabetics, is treated by using sulfonyl urea compounds, sulfonyl amide compounds and biguanide compounds in combination with dietetics, but these agents cause severe hypoglycemia, due to an overstrong blood sugar-lowering effect, and hevatitic disorders.

In view of the above disadvantageous circumstances, the present inventors carried out research into the development of oral pharmaceuticals for the treatment of the diabetics, which do not have the above-mentioned drawbacks, and found 2-phenylbenzoxepin derivatives having an advantageous blood sugar lowering activity and inhibiting activity of platelet aggregation activity (Japanese Patent Application No. 63-107972).

SUMMARY OF THE INVENTION

Accordingly, an object of the present invention is to provide novel benzoxepin derivatives having a very good blood sugar lowering activity and inhibiting activity of platelet aggregation activity, but surprisingly, not exhibiting a side effect such as a sleep-prolonging action.

More specifically, the present invention provides a benzoxepin derivative represented by the formula (I):

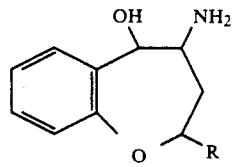

wherein R represents a heterocyclyl group, and salts thereof.

The present invention also provides a process for the production of the benzoxepin derivative of the formula (I) comprising the steps of:
reducing an oxime represented by the formula (V):

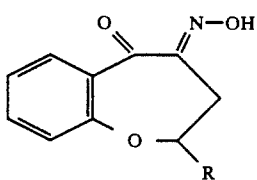

wherein R has the some meaning as defined in the formula (I); and hydrolyzing the intermediate product of the above reduction.

Moreover, the present invention provides a pharmaceutical preparation for lowering a blood sugar level comprising the benzoxepin derivative of the formula (I) or a salt thereby and a pharmaceutically acceptable carrier.

The present invention still further provides a pharmaceutical preparation for inhibiting platelet aggregation, comprising the benzoxepin derivative of the formula (I) or a salt thereof, and a pharmaceutically acceptable salt thereof.

DESCRIPTION OF THE PREFERRED EMBODIMENT

The heterocyclyl group represented by R is, for example, a pyridyl group, a pyrazinyl group, a pyrimidinyl group, pyridazinyl group, a pyrrolyl group, an imidazolyl group, a furyl group or a thienyl group.

Preferably, the substituent R is a pyridyl group such as a 2-pyridyl, 3-pyridyl or 4-pyridyl group, or a pyrazinyl group.

The acids of the benzoxepin derivative (I) are, for example, acid addition salts, for example, salts of an inorganic acid such as hydrochloric acid, hydrogen bromide, hydrogen iodide, sulfuric acid or of nitric acid, an organic acid such as formic acid, acetic acid, propionic acid, or an organic sulfonic acid such as benzene sulfonic acid or toluene sulfonic acid.

The present benzoxepin derivatives (I) can be produced, for example, as follows.

First, according to the same procedure for the synthesis of the compound represented by the formula (III), wherein R represents a phenyl group, as described in P. Bennett et al., J. Chem. Soc. Parkin. Trans. I, (12) 2990 (1979), a compound represented by the formula (II):

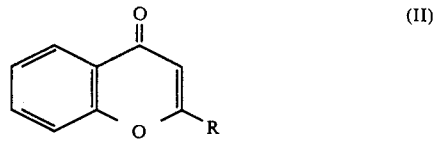

wherein R has the same meaning as defined under the formula (I), is subjected to a cyclopropanation reaction using a cyclopropanation agent such as trimethylsulfoxonium iodide or trimethylsufonium iodide in a medium such as dimethylsulfoxide, N,N-dimethylformamide or tetrahydro, at a temperature of, for example, 20° C. to 50° C., preferably 20° C. to 25° C., to obtain a oxabicycloheptane derivative represented by the formula (III):

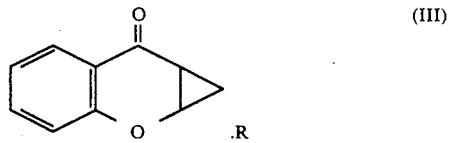

wherein R has the same meaning as defined under the formula (I).

Next, the compound (III) is treated with tri-n-butylzinhydride or azobisisobutyronitrile in an inert solvent such as benzene or toluene to obtain an oxepin derivative represented by the formula (IV):

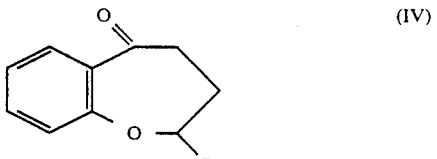

wherein R has the same meaning as defined under the formula (I).

The compound (IV) is then reacted with n-butylnitrite under the presence of hydrogen chloride in an inert solvent such as tetrahydrofuran, ethyl ether, methylene chloride, or a mixture thereof, to obtain an oxime represented by the formula (V):

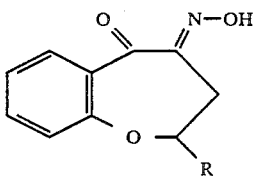

(V)

wherein R has the same meaning as described under the formula (I).

Finally, this oxime (V) is reduced and the reduced product is then hydrolyzed under an alkaline condition to obtain a benzoxepin derivative of the present invention represented by the formula (I):

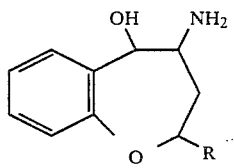

(I)

wherein R has the same meaning as defined above, in a form of a mixture of steric isomers. Preferably, the above-mentioned reduction is carried out in two steps, i.e., reduction by zinc powder/acetic acid/ammonium acetate in acetic anhydride, followed by reduction using sodium borohydride in a solvent such as methanol, ethanol, 2-propanol, or diglyme.

The mixture of steric isomers can be separated to four steric isomers, by a conventional procedure or a combination thereof, such as silica gel chromatography and recrystallization.

EXAMPLES

The present invention will now by further illustrated by, but is by no means limited to, the following Examples and Reference Examples.

Note, the physico-chemical properties of compounds prepared in the Examples and Reference Examples are shown in the Tables. Where a mixture of steric isomers can be separated, the physico-chemical properties of each isolated isomer, which isomers are labeled "a", "b", "c", and "d", are shown in the Tables.

Example 1

4-amino-5-hydroxy-2-(2-pyridyl)-2,3,4,5-tetrahydro-1-benzoxepin (Compounds 1a, 1b and 1c)

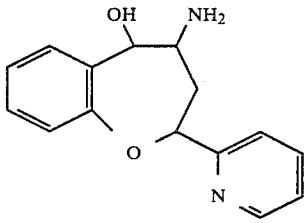

First, 894 mg (3 mmole) of 4-acetylamino-5-hydroxy-2(2-pyridyl)-2,3,4,5-tetrahydro-1-benzoxepin prepared in Reference Example 5 was dissolved in 30 ml of methanol, then 30 ml of 10% sodium hydroxide aqueous solution was added thereto, and the mixture was heated to reflux. After evaporating off the methanol, the residue was extracted with methylene chloride, and the extract dried over anhydrous magnesium sulfate. After filtration of the mixture, the filtrate was concentrated and the residue was applied to a silica gel column which was then eluted with methylene chloride/methanol (20:1) to obtain 719 mg (yield 93.6%) of the title compound 1a.

Similarly, compound 1b (yield 92.8%%) and compound 1c (yield 97.7%) were obtained from compound 9b and compound 9c in Reference Example 5, respectively.

EXAMPLE 2

4-amino-5-hydroxy-2-(3-pyridyl)2,3,4,5-tetrahydro-1-benzoxepin (Compounds 2a, 2b, and b 2c)

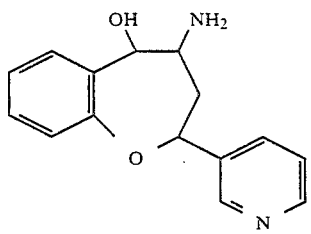

In the same manner as described in Example 1, compound 2a (yield 93.8%) and compound 2b (yield 95.6%) were obtained from compounds 14a and 14b in Reference Example 10, respectively. Further, a mixture of the compounds 2b and 2c was obtained from a mixture of compounds 14b and 14c in Reference Example 10, and the mixture was subjected to recrystallization in methylene chloride to obtain a compound 2c (yield 15.1%) as crystal.

EXAMPLE 3

4-amino-5-hydroxy-2-(4-pyridyl)2,3,4,5-tetrahydro-1-benzoxepin (Compounds 3c and 3d)

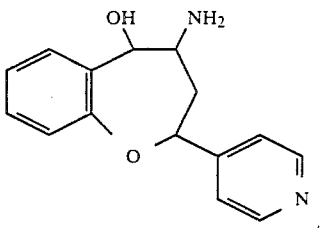

In the same manner as described in Example 1, a mixture of compounds 3a and 3d was obtained from compound 19a in Reference Example, and the mixture was subjected to recrystallization to obtain a compound 3d (yield 35.0%) as a crystal. On the other hand, a mixture of compounds 3b and 3c was obtained from compound 19b in Reference Example and the mixture was subjected to recrystallization in methylene chloride to obtain a compound 3c (yield 31.3%) as a crystal.

EXAMPLE 4

4-amino-5-hydroxy-2-pyrazinyl-2,3,4,5-tetrahydro-1-benzoxepin (Compound 4c)

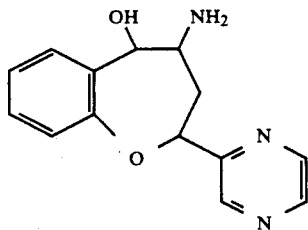

In the same manner as described in Example 1, compound 4c (yield 95.7%) was obtained from compound 24c in Reference Example 20.

REFERENCE EXAMPLES

The starting materials used in the Examples described above were prepared as described in the following Reference Examples.

REFERENCE EXAMPLE 1

3,4-benzo-5-oxo-1-(2-pyridyl)-2-oxabicyclo[4,1,0-]heptane (Compound 5)

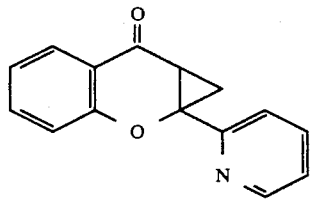

First, 9 g (225 mmoles) of 60% sodium hydride was suspended in 150 ml of dimethylsulfoxide, 49.5 g (225 mmoles) of trimethylsulfoxonium iodide was then added in portions thereto, and the mixture was stirred at a room temperature for one hour. Next a solution of 33.5 g (150 mmoles) of 4-oxo-2-(2-pyridyl)-1-benzopyran in 300 ml of dimethylsulfoxide was added to the reaction mixture, and the mixture was stirred at a room temperature for 5 hours. The reaction mixture was poured over 1 liter of ice water, and the whole was extracted three times with 500 ml of diethyl ether. The extract was washed with saturated sodium chloride aqueous solution, dried over anhydrous magnesium sulfate, and filtered. The filtrate was concentrated, and the residue applied to a silica gel column, which was then eluted with methylene chloride/ethyl acetate (4:1) to obtain 18.2 g (yield 51.2%) of the title compound.

REFERENCE EXAMPLE 2

2-(2-pyridyl)-2,3,4,5-tetrahydro-1-benzoxepin-5-one (Compound 6)

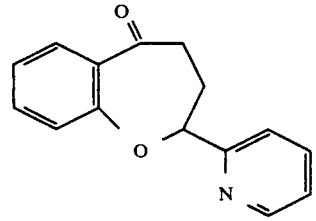

First, 14.4 g (60 mmoles) of 3,4-benzo-5-oxo-1-(2-pyridyl)-2-oxabicyclo[4,1,0]heptane were dissolved in 300 ml of benzene, 17.7 ml (66 mmoles) of tri-n-butyltin-hydride and 4.92 g (30 mmoles) of azobisisobutylonitrile were then added thereto, and the mixture was heated to reflux for 2 hours. After cooling, the reaction mixture was washed with water, dried over anhydrous magnesium sulfate, and filtered. The filtrate was concentrated, and the residue applied to a silica gel column, which was then eluted with hexane/ethyl acetate (2:1) to obtain 12.6 g (yield 88.1%) of the title compound.

REFERENCE EXAMPLE 3

4-hydroxyimino-2-(2-pyridyl)2,3,4,5-tetrahydro-1-benzoxepin-5-one (Compound 7)

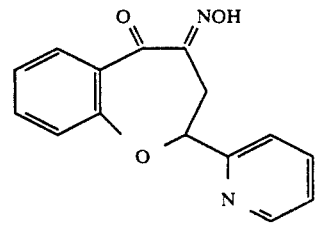

First, 10.8 g (45 mmoles) of 2-(2-pyridyl)-2,3,4,5-tetrahydro-1-benzoxepin-5-one prepared in Reference Example 2 was dissolved in a mixture of 200 ml of methylene chloride and 150 ml of tetrahydrofuran, 15 ml of ethyl ether saturated with hydrogen chloride was added thereto, and the mixture then cooled to 0° C. Next, 16 ml (135 mmoles) of n-butyl nitrite was dropwise added to the mixture, and the mixture was allowed to stand in a freezer at −15° C. to −20° C. for 24 hours. The mixture was then concentrated, and water was added to the residue. The mixture was alkalized with 1N sodium hydroxide aqueous solution and extracted with methylene chloride, and the extract was then dried over anhydrous magnesium sulfate and filtered. The filtrate was concentrated, and the residue was applied to a silica gel column, which was then eluted with methylene chloride/ethyl acetate (2:1) to obtain 9.45 g (yield 78.4%) of the title compound.

REFERENCE EXAMPLE 4

4-N-acetylamino-2-(2-pyridyl)-2,3,4,5-tetrahydro-1-benzoxepin-5-one (Compounds 8a and 8b)

First, 8.84 g (33 mmoles) of 4-hydroxyimino-2-(2-pyridyl)-2,3,4,5-tetrahydro-1-benzoxepin-5-one prepared in Reference Example 3 were dissolved in 330 ml of acetic anhydride, 6.40 g (99 mmoles) of zinc powder and 7.62 g (99 mmoles) of ammonium acetate were added thereto, and 5.7 ml (99 mmoles) of acetic acid was dropwise added to the mixture at a room temperature. The reaction mixture was stirred at a room temperature for 2 hours, and then concentrated. The residue was dissolved in ethyl acetate/methylene chloride (2:1) and filtered to remove zinc powder. The filtrate was washed with sodium bicarbonate aqueous solution and saturated sodium chloride aqueous solution, and dried over anhydrous magnesium sulfate. After filtration, the filtrate was concentrated, and the residue was applied to a silica gel column, which was then eluted with methylene chloride/methanol (30:1) to obtain 9.6 g (yield 87.0%) of the title compounds as a mixture of steric isomers 8a and 8b (ratio 2:1). The mixture was then subjected to crystallization in ethyl acetate to obtain 4.2 g of a crystal (Compound 8a) and 4.3 g of a mother liquid residue containing the compounds 8a and 8b at a ratio of 1:2.

REFERENCE EXAMPLE 5

4-N-acetylamino-5-hydroxy-2-(2-pyridyl)-2,3,4,5-tetrahydro-1-benzoxepin (Compounds 9a, 9b and 9c)

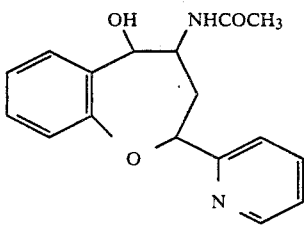

First, 2.96 g (10 mmoles) of 4-N-acetylamino-2-(pyridyl)-2,3,4,5-tetrahydro-1-benzoxepin-5-one (Compound 8a) prepared in Reference Example 4 were dissolved in 100 ml of methanol, 491 mg (13 mmoles) of sodium borohydride added thereto at $-20°$ C., and the mixture stirred for 4 hours. To the reaction mixture was added an ammonium chloride aqueous solution, and the mixture was concentrated. Water was added to the residue, and the mixture was extracted with methylene chloride. The extract was dried over anhydrous magnesium sulfate, filtered and concentrated. The residue was applied to a silica gel column, which was then eluted with methylene chloride/methanol (20:1) to obtain stereoisomers 9a and 9b of the title compounds at amounts of 910 mg (yield 30.5%) and 1.83 g (yield 61.4%), respectively. The same procedure was repeated using a mixture of stereoisomers 8a and 8b (1:2) prepared in Reference Example 3, to obtain a mixture of stereoisomers 9a, 9b and 9c of the title compounds. The mixture was then separated by column chromatography using silica gel/methylene chloride-methanol (10:1) to obtain compound 9c.

REFERENCE EXAMPLE 6

3,4-benzo-5-oxo-1-(3-pyridyl)-2-oxabicyclo[4,1,0]heptane (Compound 10)

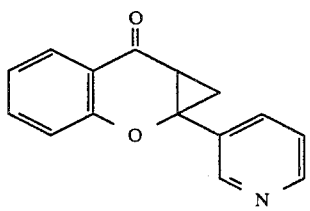

The title compound was synthesized according to the same procedure as described in Reference Example (yield 55.8%).

REFERENCE EXAMPLE 7

2-(3-pyridyl)-2,3,4,5-tetrahydro-1-benzoxepin-5-one (Compound 11)

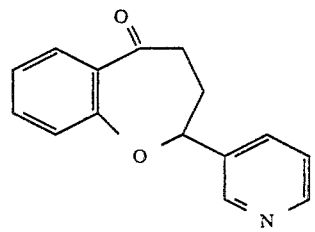

The title compound was synthesized according to the same procedure as described in Reference Example 2 (yield 71.4%).

REFERENCE EXAMPLE 8

4-hydroxyimino-2-(3-pyridyl)-2,3,4,5-tetrahydro-1-benzoxepin-5-one (Compound 12)

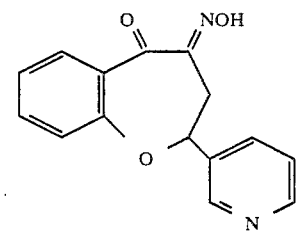

The title compound was synthesized according to the same procedure as described in Reference Example 3 (yield 66.0%).

REFERENCE EXAMPLE 9

4-N-acetylamino-2-(3-pyridyl)-2,3,4,5-tetrahydro-1-benzoxepin-5-one (Compounds 13a and 13b)

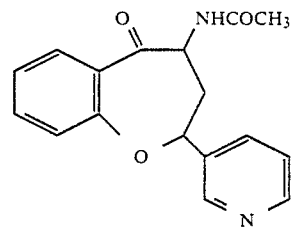

The title compounds were synthesized according to the same procedure as described in Reference Example 4, and a mixture of stereoisomers 13a and 13b (ratio of 13a:13b=2.3:1) was obtained. The mixture was subjected to crystallization in ethyl acetate to obtain a crystal (13a) and a mother liquid residue (13a:13b=1:1).

REFERENCE EXAMPLE 10

4-N-acetylamino-5-hydroxy-2-(3-pyridyl)-2,3,4,5-tetrahydro-1-benzoxepin (Compounds 14a, 14b and 14c)

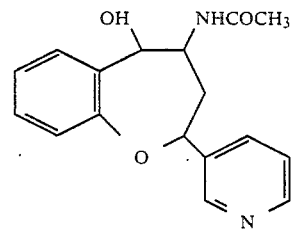

According to the same procedure as described in Reference Example 5, but starting from compound 13a prepared in Reference Example 9, stereoisomers 14a and 14b of the title compounds were obtained at yields of 56.2% (14a) and 27.1% (14b). Moreover, starting from a mixture of sterieoisomers (13a:13b=1:1) prepared in Reference Example 9, a mixture of stereoisomers 14a, 14b and 14c of the title compounds was obtained. The mixture was subjected to column chromatography according to the same procedure as in Reference Example 5, to obtain a mixture of stereoisomers 14b and 14c (ratio 2:3).

REFERENCE EXAMPLE 11

3,4-benzo-5-oxo-1-(4-pyridyl)-2-oxabicyclo[4,1,0]heptan (Compound 15)

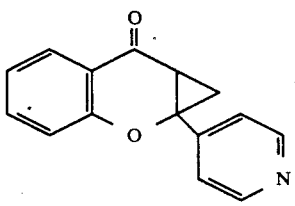

The title compound was synthesized according to the same procedure as described in Reference Example 1 (yield 46.1%).

REFERENCE EXAMPLE 12

2-(4-pyridyl)-2,3,4,5-tetrahydro-1-benzoxepin-5-one (Compound 16)

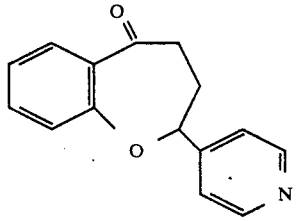

The title compound was synthesized according to the same procedure as described in Reference Example 2 (yield 89.1%).

REFERENCE EXAMPLE 13

4-hydroxyimino-2-(4-pyridyl)-2,3,4,5-tetrahydro-1-benzoxepin-5-one (Compound 17)

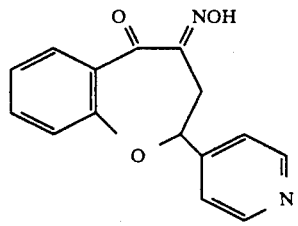

The title compound was synthesized according to the same procedure as described in Reference Example 3 (yield 53.0%).

REFERENCE EXAMPLE 14

4-N-acetylamino-2-(4-pyridyl)-2,3,4,5-tetrahydro-1-benzoxepin-5-one (Compounds 18a and 18b)

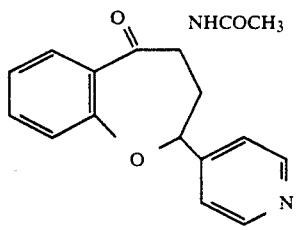

The same procedure as described in Reference Example 4 was repeated to obtain a mixture of stereoisomers 18a and 18b (ratio 3:1) of the title compounds. The mixture was subjected to crystallization in ethyl acetate to obtain a crystal (18a) and a mother liquid residue (18a:18b=2:1).

REFERENCE EXAMPLE 15

4-N-acetylamino-5-hydroxy-2-(4-pyridyl)-2,3,4,5-tetrahydro-1-benzoxepin (Compounds 19a and 19b)

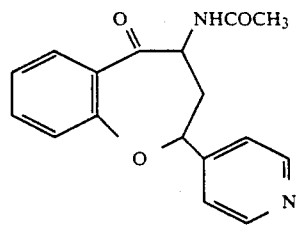

According to the same procedures described in Reference Example 5, but starting from compound 18a prepared in Reference Example 14, stereoisomers 19a (yield 63.2%) and 19b (yield 35.6%) of the title compounds were obtained.

REFERENCE EXAMPLE 16

3,4-benzo-5-oxo-1-pyrazinyl-2-oxabicyclo[4,1,0]heptane (Compound 20)

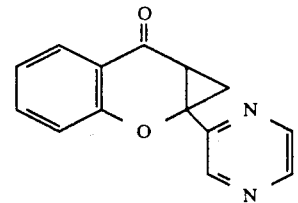

The title compound was synthesized according to the same procedure as described in Reference Example 1 (yield 40.3%).

REFERENCE EXAMPLE 17

2-pyrazinyl-2,3,4,5-tetrahydro-1-benzoxepin-5-one (Compound 21)

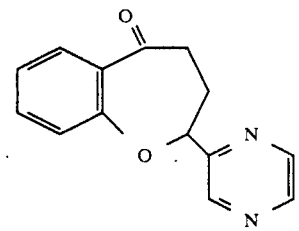

The title compound was synthesized according to the same procedure as described in Reference Example 2 (yield 62.5%).

REFERENCE EXAMPLE 18

4-hydroxyimino-2-pyrazinyl-2,3,4,5-tetrahydro-1-benzoxepin-5-one (Compound 22)

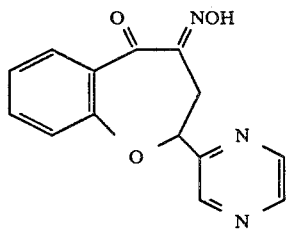

The title compound was synthesized according to the same procedure as described in Reference Example 3 (yield 49.1%).

REFERENCE EXAMPLE 19

4-N-acetylamino-2-pyrazinyl-2,3,4,5-tetrahydro-1-benzoxepin-5-one (Compounds 23a and 23b)

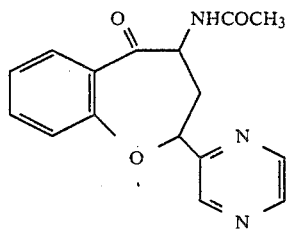

According to the same procedure as described in Reference Example 4, a mixture of stereoisomers 23a and 23b (ratio 2.5:1) of the title compounds was obtained at a total yield of 75.8%. The mixture was subjected to crystallization in ethyl acetate, to obtain crystal (23a) and a mother liquid residue (23a:23b=1:1.2).

REFERENCE EXAMPLE 20

4-N-acetylamino-5-hydroxy-2-pyrazinyl-2,3,4,5-tetrahydro-1-benzoxepin (Compound 24c)

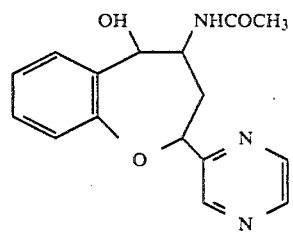

According to the same procedure as described in Reference Example 5, but starting from a mixture of stereoisomers 23a and 23b (1:1.2) prepared in Reference Example 19, a mixture of sterieoisomers was obtained. The mixture was subjected to recrystallization in ethyl acetate to obtain the title compound 24c at a yield of 39.2%.

Physico-Chemical Properties of Compounds

| Structural Formula | Compound No. | Appearance or Melting Point (°C.) | IR (cm$^{-1}$) | $^1$H-NMR δ: (TMS/CDCl$_3$) |
|---|---|---|---|---|
| (structure with OH, NH$_2$, pyridyl 3',4',5',6') | 1a | 88–90° C. | 3500–3000, 1590 1480, 1440 1370, 1220 1065, 770 | 1.8–2.2(b, 3H, O<u>H</u>, N<u>H</u>$_2$), 2.26(m, 1H, H-3α), 2.44 (m, 1H, H-3β), 3.49(m, 1H, H-4), 4.93(dd, 1H, J=2.0Hz, 10.6Hz, H-5), 5.16(d, 1H, J=2.0Hz, H-2), 7.02(dd, 1H, J=1.3Hz, 7.3Hz, H-9), 7.13–7.26(m, 3H, H-7, H-8, H-4'), 7.56(dd, 1H, J=1.3Hz, 6.6Hz, H-6), 7.65–7.79(m, 2H, H-3', H-5'), 8.55(d, 1H, J=4.6Hz, H-6') |
| | 1b | Oil | 3500–3000, 1595 1490, 1460 1440, 1300 1020, 760 | 2.12–2.40(m, 4H, O<u>H</u>, N<u>H</u>$_2$, H-3α), 2.60(m, 1H, H-3β), 3.47(m, 1H, H-4), 4.76(d, 1H, J=6.6Hz, H-5), 5.22(dd, 1H, J=2.0Hz, 11.2Hz, H-2), 7.02–7.23(m, 4H, H-7, H-8, H-9, H-5'), 7.42(dd, 1H, J=1.3Hz, 7.3Hz, H-6), 7.65–7.74(m, 2H, H-3', H-4'), 8.53 (d, 1H, J=5.9Hz, H-6') |
| | 1c | 165–167° C. | 3500–2700, 1590 1560, 1480 1430, 1220 1060, 965 770 | 1.40–2.00(b, 3H, O<u>H</u>, N<u>H</u>$_2$), 2.11(m, 1H, H-3α), 2.72(m, 1H, H-3β), 2.85(m, 1H, H-4), 4.64–4.72 (m, 2H, H-2, H-5), 7.04(m, 1H, H-9), 7.18–7.24(m, 3H, H-7, H-8, H-5'), 7.72–7.81(m, 3H, H-6, H-3', H-4'), 8.56(d, 1H, J=4.6Hz, H-6') |

-continued

Physico-Chemical Properties of Compounds

| Structural Formula | Compound No. | Appearance or Melting Point (°C.) | IR (cm$^{-1}$) | $^1$H-NMR δ: (TMS/CDCl$_3$) |
|---|---|---|---|---|
| (structure: OH, NH$_2$ on bicyclic with O, pyridin-3-yl at 3'-position) | 2a | 148–150° C. | 3300–3000, 1595 1575, 1480 1440, 1370 1210, 1055 1040, 1010 770 | 2.05–2.30(m, 4H, OH, NH$_2$, H-3α), 2.45(m, 1H, H-3β), 3.51(b, s, 1H, H-4), 4.91(dd, 1H, J=2.0Hz, 10.6Hz, H-5), 5.17(d, 1H, J=2.0Hz, H-2), 7.01 (dd, 1H, J=1.3Hz, 7.3Hz, H-9), 7.13–7.35(m, 3H, H-7, H-8, H-5'), 7.54(dd, 1H, J=1.3Hz, 6.6Hz, H-6), 7.80 (m, 1H, H-4'), 8.54(dd, 1H, J=1.3Hz, J=4.6Hz, H-6'), 8.67(d, 1H, J=2.0Hz, H-2') |
|  | 2b | Oil | 3600–2400, 1590 1480, 1460 1430, 1220 760 | 1.95(m, 1H, H-3α), 2.10–2.40(b, 3H, OH, NH$_2$), 2.67(m, 1H, H-3β), 3.50(m, 1H, H-4), 4.79(d, 1H, J=7.3Hz, H-5), 5.20(dd, 1H, J=2.0Hz, 11.6Hz, H-2), 6.99(dd, 1H, J=1.3Hz, 7.9Hz, H-9), 7.08–7.33(m, 3H, H-7, H-8, H-5'), 7.41(dd, 1H, J=2.0Hz, 7.3Hz, H-6), 7.78(m, 1H, H-4'), 8.54(dd, 1H, J=1.3Hz, 4.6Hz, H-6'), 8.66(d, 1H, J=2.0Hz, H-2') |
|  | 2c | 168–169° C. | 3500–2500, 1570 1480, 1420 1260, 1220 1060, 1030 990, 760 | 1.20–2.00(b, 3H, OH, NH$_2$), 2.24(m, 1H, H-3α), 2.37(m, 1H, H-3β), 2.86(m, 1H, H-4), 4.64–4.69 (m, 2H, H-2, H-5), 6.99(dd, 1H, J=1.3Hz, 7.3Hz, H-9), 7.19–7.22(m, 2H, H-7, H-8), 7.34(dd, 1H, J=4.6Hz, 7.9Hz, H-5'), 7.75–7.84(m, 2H, H-6, H-4'), 8.58(dd, 1H, J=2.0Hz, 4.6Hz, H-6'), 8.65(d, 1H, J=2.0Hz, H-2') |
| (structure: OH, NH$_2$ on bicyclic with O, pyridin-4-yl) | 3c | 176–178° C. | 3400–2600, 1600 1580, 1485 1230, 1070 1040, 1010 770 | 1.40–1.80(b, 3H, OH, NH$_2$), 2.11(m, 1H, H-3α), 2.38(m, 1H, H-3β), 2.85(m, 1H, H-4), 4.59–4.67 (m, 2H, H-5, H-2), 6.99(m, 1H, H-9), 7.19–7.22(m, 2H, H-7, H-8), 7.37(m, 2H, H-5', H-3'), 7.77(m, 1H, H-6), 8.63(m, 2H, H-2', H-6') |
|  | 3d | 187–189° C. | 3400–2500, 1600 1490, 1410 1250, 1230 1210, 1050 1000, 920 760 | 1.70–2.00(b, 3H, OH, NH$_2$), 2.11(dd, 1H, J=2.6Hz, 4.5Hz, H-3α), 2.35(m, 1H, H-3β), 3.34(m, 1H, H-4), 4.70(d, 1H, J=2.0Hz, H-5), 4.84(d, 1H, J=10.5Hz, H-2), 7.01–7.33(m, 4H, H-6, H-7, H-8, H-9), 7.37 (d, 2H, J=5.9Hz, H-3', H-5'), 8.62(d, 2H, J=5.9Hz, H-2', H-6') |
| (structure: OH, NH$_2$ on bicyclic with O, pyrazinyl) | 4c | 141–143° C. | 3400–2900, 1580 1480, 1400 1260, 1220 1080, 1065 1015, 760 730 | 1.30–1.80(b, 3H, OH, N$\underline{H}_2$), 2.16(m, 1H, H-3α), 2.71(m, 1H, H-3β), 2.86(m, 1H, H-4), 4.66(d, 1H, J=9.2Hz, H-5), 4.77(d, 1H, J=10.6Hz, H-2), 7.06(m, 1H, H-9), 7.19–7.25(m, 2H, H-7, H-8), 7.80(m, 1H, H-6), 8.53–8.57(m, 2H, H-5', H-6'), 9.04(s, 1H, H-3') |
| (structure: tricyclic with O=, O, cyclopropane, pyridin-2-yl, numbered 1–11) | 5 | Oil | 1670 1605, 1580 1460, 1380 1320, 1235 1130, 975 775, 755 | 1.73(t, 1H, J=6.6Hz, H-6), 2.48(dd, 1H, J=6.6Hz, 10.6Hz, H-7), 2.88(dd, 1H, J=6.6Hz, 10.6Hz, H-7), 7.08–7.28(m, 1H, H-8, H-10, H-5'), 7.56(m, 1H, H-9), 7.77(m, 1H, H-4'), 7.86(d, 1H, J=7.9Hz, H-3'), 7.95(d, 1H, J=7.9Hz, H-11), 8.54(d, 1H, J=4.6Hz, H-6') |
| (structure: tricyclic with O=, O, cyclopropane, pyridin-3-yl) | 10 | Oil | 1660 1600, 1575 1460, 1380 1320, 1230 1130, 1105 1020, 970 800, 760 700 | 1.82(t, 1H, J=6.6Hz, H-6), 2.08(dd, 1H, J=6.6Hz, 10.6Hz, H-7), 2.56(dd, 1H, J=6.6Hz, 10.6Hz, H-7), 7.05–7.14(m, 2H, H-8, H-10), 7.37(dd, 1H, J=4.6Hz, 7.9Hz, H-5'), 7.54(m, 1H, H-9), 7.79(m, 1H, H-4'), 7.93(dd, 1H, J=2.0Hz, 7.9Hz, H-11), 8.62 (m, 1H, H-6'), 8.75(d, 1H, J=2.0Hz, H-2') |

-continued

Physico-Chemical Properties of Compounds

| Structural Formula | Compound No. | Appearance or Melting Point (°C.) | IR (cm$^{-1}$) | $^1$H-NMR δ: (TMS/CDCl$_3$) |
|---|---|---|---|---|
| | 15 | 138–140° C. | 1670 1600<br>1465 1370<br>820 750 | 1.87(dd, 1H, J=7.3Hz, 6.6Hz, H-6), 2.06(dd, 1H, J=7.3Hz, 11.2Hz, H-7), 2.60(dd, 1H, J=6.6Hz, 11.2Hz, H-7), 7.10–7.15(m, 2H, H-9, H-10), 7.30(m, 2H, H-3', H-5'), 7.56(m, 1H, H-9), 7.93(dd, 1H, J=2.0Hz, 7.9Hz, H-11), 8.65(m, 2H, H-2', H-6') |
| | 20 | 105–107° C. | 1675 1610<br>1470 1380<br>1320 1235<br>1135 970<br>845 770 | 1.79(t, 1H, J=6.6Hz, H-6), 2.39(dd, 1H, J=6.6Hz, 10.6Hz, H-7), 2.86(dd, 1H, J=6.6Hz, 10.6Hz, H-7), 7.11–7.18(m, 2H, H-9, H-10), 7.57(m, 1H, H-9), 7.95(dd, 1H, J=2.0Hz, 7.9Hz, H-11), 8.50(m, 2H, H-5', H-6'), 9.14(d, 1H, J=1.3Hz, H-3') |
| | 6 | Oil | 1680 1595<br>1570 1470<br>1450 1285<br>1220 980<br>760 | 2.57(m, 2H, H-3), 2.80(m, 1H, H-4), 3.10(m, 1H, H-4), 5.19(dd, 1H, J=6.6Hz, 8.6Hz, H-2), 7.11–7.19 (m, 2H, H-7, H-9), 7.25(dd, 1H, J=4.6Hz, 7.9Hz, H-5'), 7.45(m, 1H, H-8), 7.63(d, 1H, J=7.9Hz, H-3'), 7.77(m, 1H, H-4'), 7.84(dd, 1H, J=2.0Hz, 7.9Hz, H-6), 8.59(d, 1H, J=4.6Hz, H-6') |
| | 11 | Oil | 1680 1600<br>1475 1450<br>1420 1280<br>1220 | 2.38–2.50(m, 2H, H-3), 2.84(m, 1H, H-4), 3.16(m, 1H, H-4), 5.13(dd, 1H, J=6.6Hz, 8.9Hz, H-2), 7.06 (d, 1H, J=7.9Hz, H-9), 7.16(m, 1H, H-7), 7.34(dd, 1H, J=4.6Hz, 7.9Hz, H-5'), 7.45(m, 1H, H-8), 7.78 (m, 1H, H-4'), 7.83(dd, 1H, J=2.0Hz, 7.9Hz, H-6), 8.59(dd, 1H, J=2.0Hz, 4.6Hz, H-6'), 8.68(d, 1H, J=2.0Hz, H-2') |
| | 16 | Oil | 1680 1600<br>1475 1460<br>1415 1290<br>1220 980<br>815 760 | 2.29–2.57(m, 2H, H-3), 2.86(m, 1H, H-4), 3.12(m, 1H, H-4), 5.08(dd, 1H, J=5.3Hz, 10.5Hz, H-2), 7.10–7.20(m, 2H, H-9, H-7), 7.40(d, 2H, J=5.3Hz, H-3', H-5'), 7.45(m, 1H, H-8), 7.84(dd, 1H, J=1.3Hz, 7.9Hz, H-6), 8.65(d, 2H, J=5.3Hz, H-2', H-6') |
| | 21 | Oil | 1690 1605<br>1480 1460<br>1410 1290<br>1220 1150<br>980 760 | 2.54–2.64(m, 2H, H-3), 2.85(m, 1H, H-4), 3.12(m, 1H, H-4), 5.26(dd, 1H, J=5.9Hz, 9.2Hz, H-2), 7.11–7.22 (m, 2H, H-7, H-9), 7.47(m, 1H, H-8), 7.85)dd, 1H, J=2.0Hz, 7.9Hz, H-6), 8.57(m, 2H, H-5', H-6'), 8.96(d, 1H, J=1.3Hz, H-3') |

-continued

Physico-Chemical Properties of Compounds

| Structural Formula | Compound No. | Appearance or Melting Point (°C.) | IR (cm⁻¹) | ¹H-NMR δ: (TMS/CDCl₃) |
|---|---|---|---|---|
| (benzoxepinone with =NOH, 2-pyridyl) | 7 | 205–207° C. | 3000–2500 1665 1595 1470 1310 1005 930 780 750 | 3.38(dd, 1H, J=4.6Hz, 13.9Hz, H-3α), 3.72(dd, 1H, J=6.6Hz, 13.9Hz, H-3β), 5.74(dd, 1H, J=4.6Hz, 6.6Hz, H-2), 7.15(d, 1H, J=8.6Hz, H-9), 7.23(m, 1H, H-7), 7.49–7.60(m, 2H, H-8, H-5'), 7.82(m, 1H, H-4'), 7.91–8.05(m, 2H, H-6, H-3'), 8.70(d, 1H, J=4.6Hz, H-6') |
| (benzoxepinone with =NOH, 3-pyridyl) | 12 | 170–172° C. | 3000–2400 1660 1590 1470 1300 1270 1240 1020 935 780 | 3.25(dd, 1H, J=4.0Hz, 17.2Hz, H-3α), 3.59(dd, 1H, J=9.2Hz, 17.2Hz, H-3β), 5.43(dd, 1H, J=4.0Hz, 9.2Hz, H-2), 7.06(d, 1H, J=8.6Hz, H-9), 7.19(m, 1H, H-7), 7.39(dd, 1H, J=5.3Hz, 7.9Hz, H-5'), 7.52(m, 1H, H-8), 7.83(m, 1H, H-4'), 8.00(dd, 1H, J=1.3Hz, 7.9Hz, H-6), 8.62(dd, 1H, J=1.3Hz, 5.3Hz, H-6'), 8.75(d, 1H, J=2.0Hz, H-2) |
| (benzoxepinone with NOH, 4-pyridyl) | 17 | 215–217° C. | 3000–2500 1670 1615 1600 1475 1455 1320 1270 1010 940 | 3.26(dd, 1H, J=2.6Hz, 17.9Hz, H-3α), 3.55(dd, 1H, J=9.9Hz, 17.9Hz, H-3β), 5.49(dd, 1H, J=2.6Hz, 9.9Hz, H-2), 7.12(d, 1H, J=8.7Hz, H-9), 7.20(m, 1H, H-7), 7.51–7.58(m, 3H, H-8, H-3', H-5'), 7.97(dd, 1H, J=1.3Hz, 7.3Hz, H-6), 8.68(d, 2H, 5.3Hz, H-2', H-6') |
| (benzoxepinone with =NOH, pyrazinyl) | 22 | 198–200° C. | 3100–2800 1675 1600 1470 1440 1300 1220 1010 925 880 750 | 3.46(dd, 1H, J=4.0Hz, 17.2Hz, H-3α), 3.64(dd, 1H, J=9.2Hz, 17.2Hz, H-3β), 5.55(dd, 1H, J=4.0Hz, 9.2Hz, H-2), 7.11(d, 1H, J=7.9Hz, H-9), 7.22(m, 1H, H-7), 7.54(m, 1H, H-8), 8.01(dd, 1H, J=1.3Hz, 7.9Hz, H-6), 8.60(m, 2H, H-5', H-6'), 8.98(s, 1H, H-3') |
| (benzoxepinone with NHCOCH₃, 2-pyridyl) | 8a | 171–173° C. | 3280 1690 1640 1550 1470 1455 1370 1275 1220 1030 920 780 760 | 2.04(s, 3H, COCH₃), 2.33(ddd, 1H, J=5.3Hz, 10.5Hz, 13.2Hz, H-3α), 3.23(ddd, 1H, J=7.9Hz, 11.9Hz, 13.2Hz, H-3β), 5.08(dd, J=5.3Hz, 11.9Hz, H-2), 5.31 (m, 1H, H-4), 6.68(b d, 1H, J=6.4Hz, NH), 7.13–7.27 (m, 3H, H-9, H-7, H-5'), 7.49(m, 1H, H-8), 7.74–7.80 (m, 2H, H-3', H-4'), 7.88(dd, J=1.3Hz, 7.9Hz, H-6), 8.53(d, 1H, J=4.6Hz, H-6') |
| Mixture of 8a and 8b | 8b | | | 2.06(s, 3H, COCH₃), 2.59(m, 1H, H-3α), 2.88(m, 1H, H-3β), 5.07(m, 1H, H-4), 5.68(dd, 1H, J=5.3Hz, 10.5Hz, H-2), 6.95(b, 1H, NH), 7.08–8.55(m, Ar) |
| (benzoxepinone with NHCOCH₃, 3-pyridyl) | 13a | 159–162° C. | 3300 1690 1640 1600 1550 1460 1280 1210 1100 800 760 710 | 2.05(s, 3H, COCH₃), 2.12(m, 1H, H-3α), 3.27(m, 1H, H-3β), 4.98(dd, 1H, J=5.3Hz, 12.5Hz, H-2), 5.34(m, 1H, H-4), 6.75(b, 1H, NH), 7.13–7.29(m, 3H, H-7, H-9, H-5'), 7.36(m, 1H, H-4'), 7.53(m, 1H, H-8), 7.88(m, 1H, H-6), 8.57–8.62(m, 2H, H-2', H-6') |
| Mixture of 13a and 13b | 13b | | | 2.09(s, 3H, COCH₃), 2.10–2.26(m, 1H, H-3α), 2.84 (m, 1H, H-3β), 5.08(m, 1H, H-4), 5.68(dd, 1H, |

-continued

Physico-Chemical Properties of Compounds

| Structural Formula | Compound No. | Appearance or Melting Point (°C.) | IR (cm$^{-1}$) | $^1$H-NMR δ: (TMS/CDCl$_3$) |
|---|---|---|---|---|
| | | | | J=5.3Hz, 11.9Hz, H-2), 6.92(bd, 1H, J=4.0Hz, N<u>H</u>), 7.13–8.62(m, Ar) |
| (structure: benzoxepine with NHCOCH$_3$ ketone and 4-pyridyl) | 18a | 174–177° C. | 3270 1690<br>1640 1600<br>1540 1450<br>1270 1205<br>1035 845<br>800 760<br>700 | 2.05(s, 3H, COCH$_3$), 2.13(ddd, 1H, J=5.3Hz, 9.9Hz, 13.2Hz, H-3α), 3.19(m, 1H, H-3β), 4.94(dd, 1H, J=5.3Hz, 12.5Hz, H-2), 5.31(m, 1H, H-4), 6.72(bd, 1H, J=6.6Hz, N<u>H</u>), 7.15–7.20(m, 2H, H-7, H-9), 7.36–7.38 (m, 2H, H-3', H-5'), 7.51(m, 1H, H-8), 7.88 (dd, 1H, J=2.0Hz, 7.9Hz, H-6), 8.64(m, 2H, H-2', H-6') |
| Mixture of 18a and 18b | 18b | | | 2.09(s, 3H, COCH$_3$), 2.10–2.15(m, 1H, H-3α), 2.85 (m, 1H, H-3β), 5.07(m, 1H, H-4), 5.60(m, 1H, H-2), 6.52(m, 1H, N<u>H</u>), 7.00–8.70(m, Ar) |
| (structure: benzoxepine with NHCOCH$_3$ ketone and pyrazinyl) | 23a | 165–167° C. | 3290 1690<br>1640 1555<br>1460 1280<br>1220 800<br>760 | 2.05(s, 3H, COCH$_3$), 2.33(ddd, 1H, J=5.3Hz, 10.5Hz, 13.2Hz, H-3α), 3.30(ddd, 1H, J=7.9Hz, 11.9Hz, 13.2Hz, H-3β), 5.15(dd, 1H, J=5.3Hz, 11.9Hz, H-2), 5.30(m, 1H, H-4), 6.71(bd, 1H, J=5.9Hz, N<u>H</u>), 7.17–7.24 (m, 2H, H-7, H-9), 7.53(m, 1H, H-8), 7.91(dd, 1H, J=2.0Hz, 7.3Hz, H-9), 8.52(dd, 1H, J=1.3Hz, 2.6Hz, H-6'), 8.57(d, 1H, J=2.6Hz, H-5'), 9.04(d, 1H, J=1.3Hz, H-3') |
| Mixture of 23a and 23b | 23b | | | 2.09(s, 3H, COCH$_3$), 2.56(m, 1H, H-3α), 2.90(ddd, 1H, J=5.3Hz, 3.3Hz, 14.5Hz, H-3β), 5.12(m, 1H, H-4), 5.80(dd, J=5.3Hz, 10.5Hz, H-2), 6.90(bd, 1H, J=4.6Hz, N<u>H</u>), 7.17–7.24(m, 2H, H-7, H-9), 7.41(m, 1H, H-8), 7.97(dd, 1H, J=2.0Hz, 7.9Hz, H-6), 8.44 (m, 1H, H-6'), 8.86(d, 1H, J=1.3Hz, H-3') |
| (structure: benzoxepine with OH, NHCOCH$_3$ and 2-pyridyl) | 9a | 246–248° C. | 3200 3030<br>1635 1545<br>1485 1260<br>1225 1105<br>980 780<br>750 | 1.92(s, 3H, COCH$_3$), 2.40–2.47(m, 2H, H-3), 4.54 (m, 1H, H-4), 4.82(dd, 1H, J=3.3Hz, 10.5Hz, H-2), 5.55(d, 1H, J=7.3Hz, H-5), 6.11(m, 1H, N<u>H</u>), 7.01 (dd, 1H, J=2.6Hz, 6.6Hz, H-9), 7.18–7.28(m, 3H, H-7, H-8, H-4'), 7.58(dd, 1H, J=2.6Hz, 6.6Hz, H-6), 7.75–7.78(m, 2H, H-3', H-5'), 8.49(d, 1H, J=4.6Hz, H-6') |
| | 9b | 170–172° C. | 3400 3230<br>1640 1540<br>1480 1440<br>1230 1210<br>1060 995<br>760 | 1.96(s, 3H, COCH$_3$), 2.23(m, 1H, H-3α), 2.57(m, 1H, H-3β), 4.24(b, 1H, O<u>H</u>), 4.48(m, 1H, H-4), 4.94(d, 1H, J=5.9Hz, H-5), 5.13(dd, 1H, J=1.3Hz, 11.9Hz, H-2), 6.25(d, 1H, J=7.3Hz, N<u>H</u>), 7.06–7.31(m, 4H, H-7, H-8, H-9, H-5'), 7.41(dd, 1H, J=2.0Hz, 7.3Hz, H-6), 7.69–7.81(m, 2H, H-3', H-4'), 8.46(d, 1H, J=4.6Hz, H-6') |
| | 9c | 201–203° C. | 3500–3100<br>1620 1555<br>1480 1225<br>1050 970<br>780 760<br>750 | 1.98(s, 3H, COCH$_3$), 2.33(m, 1H, H-3α), 2.61(m, 1H, H-3β), 4.19(m, 1H, H-4), 4.35(bs, 1H, OH), 5.05–5.09 (m, 2H, H-2, H-5), 6.94(bd, 1H, J=5.9Hz, N<u>H</u>), 7.03–7.33(m, 4H, H-7, H-8, H-9, H-5'), 7.63(dd, 1H, J=1.3Hz, 6.6Hz, H-6), 7.70(d, 1H, J=7.9Hz, H-3'), 7.80(m, 1H, H-4'), 8.59(d, 1H, J=4.6Hz, H-6') |

-continued

| Structural Formula | Compound No. | Appearance or Melting Point (°C.) | IR (cm⁻¹) | ¹H-NMR δ: (TMS/CDCl₃) |
|---|---|---|---|---|
| [Structure: benzoxepine with OH, NHCOCH₃, and 3-pyridyl substituents] | 14a | Oil | 3600–2900, 1650, 1550, 1490, 1220, 1050, 980, 760, 740 | 1.90(s, 3H, COC$\underline{H}_3$), 2.30–2.46(m, 2H, H-3), 3.60 (b, 1H, O$\underline{H}$), 4.53(m, 1H, H-4), 4.95(dd, 1H, J=3.3Hz, 10.5Hz, H-2), 5.26(s, 1H, H-5), 6.31(b, 1H, N$\underline{H}$), 6.97(dd, 1H, J=2.0Hz, 7.3Hz, H-9), 7.11–7.24 (m, 2H, H-7, H-8), 7.37(dd, 1H, J=4.6Hz, 7.9Hz, H-5'), 7.53(dd, 1H, J=1.3Hz, 7.3Hz, H-6), 7.88(d, 1H, J=7.9Hz, H-4'), 8.49(d, 1H, J=4.6Hz, H-6'), 8.65 (s, 1H, H-2') |
|  | 14b | 206–207° C. | 3350, 3230, 1655, 1550, 1485, 1420, 1370, 1220, 1050, 1040, 765, 710 | 1.94(s, 3H, COC$\underline{H}_3$), 2.09(m, 1H, H-3α), 2.65(m, 1H, H-3β), 4.52(m, 1$\underline{H}$, H-4), 4.85(d, 1H, J=6.6Hz, H-5), 5.01(d, 1H, J=11.2Hz, H-2), 6.16(d, 1H, J=7.9Hz, N$\underline{H}$), 6.97(d, 1H, J=7.9Hz, H-9), 7.11(m, 1H, H-7), 7.22–7.37(m, 3H, H-6, H-8, H-5'), 7.77(m, 1H, H-4'), 8.46(dd, 1H, J=1.3Hz, 4.6Hz, H-6'), 8.59(d, 1H, J=2.0Hz, H-2') |
| [Structure: benzoxepine with OH, NHCOCH₃, and 4-pyridyl substituents] | 19a | 201–212° C. | 3400–3100, 1640, 1545, 1480, 1415, 1220, 1060, 1050, 995, 800, 765 | 1.97(s, 3H, COC$\underline{H}_3$), 2.38(m, 2H, H-3), 4.07(b, 1H, O$\underline{H}$), 4.54(m, 1H, H-4), 4.83(dd, 1H, J=5.3Hz, 9.2Hz, H-2), 5.26(s, 1H, H-5), 5.78(d, 1H, J=6.6H), 7.04 (dd, 1H, J=1.3Hz, 7.9Hz, H-9), 7.10–7.30(m, 2H, H-7, H-8), 7.36(d, 2H, J=5.9Hz, H-3', H-5'), 7.54 (m, 1H, H-6), 8.61(d, 2H, J=5.9Hz, H-2', H-6') |
|  | 19b | 188–190° C. | 3300, 3150, 1650, 1550, 1480, 1450, 1375, 1220, 1060, 1000, 760 | 1.94(s, 3H, COC$\underline{H}_3$), 2.15(m, 1H, H-3α), 2.61(m, 1H, H-3β), 4.55(m, 1$\underline{H}$, H-4), 4.79(d, 1H, J=5.9Hz, H-5), 4.88(d, 1H, J=11.2Hz, H-2), 5.82(bd, 1H, J=7.3Hz, N$\underline{H}$), 7.05(dd, 1H, J=1.3Hz, 7.9Hz, H-9), 7.14(m, 1H, H-7), 7.30–7.35(m, 4H, H-6, H-8, H-3', H-5'), 8.52 (d, 2H, J=5.9Hz, H-2', H-6') |
| [Structure: benzoxepine with OH, NHCOCH₃, and pyrazinyl substituents] | 24a | Amorphous | 3600–3000, 1675, 1530, 1480, 1220, 1060, 760 | 1.91(s, 3H, COC$\underline{H}_3$) 2.39–2.50(m, 2H, H-3), 4.59 (m, 1H, H-4), 4.93(dd, 1H, J=3.3Hz, 10.5Hz, H-2), 5.10(d, 1H, J=6.6Hz, O$\underline{H}$), 5.26(d, 1H, J=6.6Hz, H-5), 5.97(dd, 1H, J=5.9Hz, N$\underline{H}$), 7.05(dd, 1H, J=1.3Hz, 7.9Hz, H-6), 7.15–7.27(m, 2H, H-7, H-8), 7.56(dd, 1H, J=2.0Hz, 7.3Hz, H-6), 8.48(d, 1H, J=2.6Hz, H-6'), 8.55(d, 1H, J=2.6Hz, H-5'), 9.01(s, 1H, H-3') |
|  | 24b | Amorphous | 3500–3000, 1650, 1550, 1480, 1220, 1060, 760 | 1.98(s, 3H, COC$\underline{H}_3$), 2.36(m, 1H, H-3α), 2.68(m, 1H, H-3β), 3.40(b, 1$\underline{H}$, O$\underline{H}$), 4.60(m, 1H, H-4), 4.87(d, 1H, J=5.9Hz, H-5), 5.07(dd, 1H, J=1.3Hz, 10.5Hz, H-2), 5.65(d, 1H, J=7.9Hz, N$\underline{H}$), 7.09–7.41(m, 4H, H-6, H-7, H-8, H-9), 8.50(m, 1$\underline{H}$, H-6'), 8.55(d, 1H, J=2.6Hz, H-5'), 9.02(d, 1H, J=1.3Hz, H-3') |
|  | 24c | 189–192° C. | 3500–3300, 1640, 1550, 1480, 1220, 1060, 760, 725 | 2.10(s, 3H, COC$\underline{H}_3$), 2.30(m, 1$\underline{H}$, H-3α), 2.73(m, 1H, H-3β), 3.57(b, 1$\underline{H}$, O$\underline{H}$), 4.29(m, 1H, H-4), 5.01(m, 1H, H-5), 5.11(dd, 1$\underline{H}$, J=3.3Hz, 10.5Hz, H-2), 5.23 (b, 1H, N$\underline{H}$), 7.07(dd, 1H, J=2.0Hz, 7.9Hz, H-6), 7.21–7.28(m, 2H, H-7, H-8), 7.63(dd, 1H, J=1.3Hz, 7.3Hz, H-6), 8.55(m, 1H, H-6'), 8.59(d, 1H, J=2.6Hz, H-5'), 8.99(d, 1H, J=1.3Hz, H-3') |

| Formulation 1. (Capsule) | |
|---|---|
| Compound 1c of Example 1 | 10 mg |
| Lactose | 59.5 mg |
| Corn starch | 80 mg |
| Light silica anhydride | 0.5 mg |
| Total | 150 mg |

The above listed materials were thoroughly mixed and then filled in a gelatin capsule by a conventional procedure.

| Formulation 2. (Tablet) | |
|---|---|
| Compound 1c of Example 1 | 10 mg |
| Lactose | 59 mg |
| Corn starch | 70 mg |

-continued

| Formulation 2. (Tablet) | |
|---|---|
| Paste of corn starch | 10 mg |
| Magnesium stearate | 1 mg |
| Total | 150 mg |

The above-listed ingredients were mixed and pressed to form a tablet, by a conventional procedure.

The blood sugar-lowering inhibiting activity of platelet aggregation action, and sleep-prolonging action of the present compounds were tested according to the following methods.

1. Blood Sugar-Lowering Activity ddy mice 5 to 6 weeks old were starved for 24 hours, and the test compound was orally administered in the form of a CMC suspension. Then 30 minutes after the administration, a blood sample was taken from the eye-ground vessel and immediately centrifuged, and the glucose concentration in serum was measured by a glucose oxidase method using a commercial kit.

2. Inhibiting Activity of Platelet-Aggregation

Platelet samples were obtained from a healthy man and a male Japanese white rabbit. Namely, blood samples were obtained from the elbow vein of the man and from the auricle artery of the rabbit, and to the blood samples were added 0.31% and 0.38% of citric acid respectively. The blood samples were centrifuged to prepare platelet-rich plasma (PRP), and the PRP was used for the measurement in the platelet aggregation test, using a permeable platelet aggregation ability analyzer (AGGREGO-METER RAM-61; Rika Denki, Japan). As aggregation-including agents, ADP (adenosine diphosphate), arachidonic acid, collagen, a platelet activating factor, epinephrine and Ca** ionophore A-23187 were used. Each test compound was dissolved in DMSO (dimethylsulfoxide), and the solution was added to the PRP.

3 Action on hexobarbital sleep

First, ddY male mice 5 weeks old were starved for 24 hours, then 70 mg/kg of hexobarbital was intraperitoneally administered to each mouse, and a time from the disappearance to the restoration of the body-righting reflex was considered the sleep time. A test compound was administered 30 minutes before the above administration.

Results

Compounds 1c, 2c, 3c, and 4c exhibited a significant blood sugar lowering activity and inhibition of platelet aggregating action, at a dose of 10 mg/kg. On the other hand, the compound 2c did not exhibit a sleep-prolonging action at doses of both 10 mg/kg p.o., and 30 mg/kg p.o., revealing that it has low central side effedts.

We claim:

1. A benzoxepin derivative represented by the formula (I):

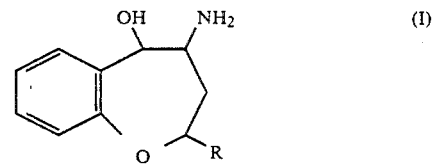

wherein R represents a heterocyclyl group selected from the group consisting of a pyridyl group, a pyrazinyl group, a pyrimidinyl group, a pyridazinyl group, a pyrrolyl group, an imidazolyl group, a furyl group and a thienyl group, and salts thereof.

2. A benzoxepin derivative according to claim 1, wherein the heterocyclic group is selected from the group consisting of 2-pyridyl, 3-pyridyl, 4-pyridyl and pyrazinyl.

3. A pharmaceutical preparation for lowering a blood sugar level comprising an effective amount of a benzoxepin derivative of the formula (I) according to claim 1 or a salt thereof, and a pharmaceutically acceptable carrier.

4. A pharmaceutical preparation for inhibiting platelet aggregation comprising an effective amount of a benzoxepin derivative of the formula (I) according to claim 1 or a salt thereof, and a pharmaceutically acceptable carrier.

* * * * *